(12) United States Patent
Senner

(10) Patent No.: US 6,528,191 B1
(45) Date of Patent: *Mar. 4, 2003

(54) APPARATUS FOR MONITORING A HYDROGEN CONTAINING GAS STREAM

(75) Inventor: Ralf Senner, Mainz (DE)

(73) Assignee: General Motors Corporation, Detroit, MI (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/416,583

(22) Filed: Oct. 12, 1999

(51) Int. Cl.$^7$ ................................................. H01M 8/00
(52) U.S. Cl. ............................ 429/12; 429/22; 429/23; 429/27; 204/424; 422/98; 422/83
(58) Field of Search .......................... 429/12, 13, 22, 429/23, 27; 204/424, 429, 421; 422/98, 94, 83

(56) References Cited

U.S. PATENT DOCUMENTS

| | | | | |
|---|---|---|---|---|
| 4,315,753 A | * | 2/1982 | Bruckenstein et al. | ......... 23/232 |
| 4,976,991 A | * | 12/1990 | Ammende et al. | ........... 427/125 |
| 5,279,169 A | * | 1/1994 | Freeman | ...................... 73/866 |
| 5,472,580 A | * | 12/1995 | Kennard, III et al. | ... 204/153.1 |
| 6,001,499 A | * | 12/1999 | Grot et al. | ..................... 429/22 |

* cited by examiner

Primary Examiner—Stephen Kalafut
Assistant Examiner—R Alejandro
(74) Attorney, Agent, or Firm—Anthony Luke Simon, Esq.; Karl F. Barr, Jr., Esq.; Linda M. Deschere, Esq.

(57) ABSTRACT

An apparatus for monitoring hydrogen and optionally a non-hydrogen gas including carbon monoxide. The apparatus includes a sensor assembly consisting of a plurality of electrochemical cells sequentially arranged in a path of the hydrogen-containing gas stream. Reaction and consumption of hydrogen at catalytically reactive surface areas of the cells generates a current which is proportional to the amount of hydrogen in the gas stream entering the sensor.

26 Claims, 6 Drawing Sheets

APPARATUS FOR MONITORING A HYDROGEN CONTAINING GAS STREAM

CROSS REFERENCE

This application discloses subject matter which is disclosed and claimed in co-pending U.S. patent application Ser. No. 09/358,080, filed on Jul. 21, 1999 now abandoned, in the names of David J. Hart-Predmore and William H. Pettit, and entitled "Methanol Tailgas Combustor Control Method," the entire contents of which are incorporated by reference.

FIELD OF THE INVENTION

This invention relates to an apparatus for monitoring a hydrogen containing gas stream.

BACKGROUND OF THE INVENTION

Fuel cells have been used as a power source in many applications. For example, fuel cells have been proposed for use in electrical vehicular power plants to replace internal combustion engines. In proton exchange membrane (PEM) type fuel cells, hydrogen is supplied to the anode of the fuel cell and oxygen is supplied as the oxidant to the cathode. PEM fuel cells include a membrane electrode assembly (MEA) comprising a thin, proton transmissive, non-electrically conductive solid polymer membrane-electrolyte having the anode on one of its faces and the cathode on the opposite face. The MEA is sandwiched between a pair of electrically conductive elements which (1) serve as current collectors for the anode and cathode, and (2) contain appropriate channels and/or openings therein for distributing the fuel cells gaseous reactants over the surfaces of the respective anode and cathode catalysts. A plurality of individual cells are commonly bundled together to form a PEM fuel cell stack. The term "fuel cell" is often used to refer to an individual cell and also may refer to a fuel cell stack which contains many individual fuel cells often on the order of one hundred or more, connected in series. Each cell within the stack includes the membrane electrode assembly (MEA), and each such MEA provides its increment of voltage. A group of cells within the stack is referred to as a cluster. Typical arrangements of multiple cells in a stack are described in U.S. Pat. No. 5,763,113, assigned to General Motors Corporation.

In PEM fuel cells, hydrogen ($H_2$) is the anode reactant (i.e., fuel) and oxygen is the cathode reactant (i.e., oxidant). The oxygen can be either a pure form ($O_2$), or air (a mixture of $O_2$ and $N_2$). The solid polymer electrolytes are typically made from ion exchange resins such as perfluoronated sulfonic acid. The anode/cathode typically comprises finely divided catalytic particles, which are often supported on carbon particles, in a mix with a proton conductive resin. The catalytic particles are typically costly precious metal particles. These membrane electrode assemblies (MEAs) which comprise the catalyzed electrodes are relatively expensive to manufacture and require certain controlled conditions in order to prevent degradation thereof.

For vehicular applications, it is desirable to use a liquid fuel such as an alcohol (e.g., methanol or ethanol), or hydrocarbons (e.g., gasoline) as the source of hydrogen for the fuel cell. Such liquid fuels for the vehicle are easy to store onboard and there is a nationwide infrastructure for supplying liquid fuels. However, such fuels must be dissociated to release the hydrogen content thereof for fueling the fuel cell. The dissociation reaction is accomplished heterogeneously within a chemical fuel processor, known as a reformer, that provides thermal energy throughout a catalyst mass and yields a reformate gas comprising primarily hydrogen and carbon dioxide. For example, in the steam methanol reformation process, methanol and water (as steam) are ideally reacted to generate hydrogen and carbon dioxide. The reforming reaction is an endothermic reaction that requires external heat for the reaction to occur.

Fuel cell systems which process a hydrocarbon fuel to produce a hydrogen-rich reformate for consumption by PEM fuel cells are known and are described in co-pending U.S. patent application Ser. No. 08/975,442 now U.S. Pat. No. 5,887,276 and Ser. No. 08/980,087, now U.S. Pat. No. 6,077,620 filed in November, 1997, and U.S. Ser. No. 09/187,125, filed in November, 1998, now U.S. Pat. No. 6,238,815 and each assigned to General Motors Corporation, assignee of the present invention. A typical PEM fuel cell and its membrane electrode assembly (MEA) are described in U.S. Pat. Nos. 5,272,017 and 5,316,871, issued respectively Dec. 21, 1993 and May 31, 1994, and assigned to General Motors Corporation.

The reforming reaction is an endothermic reaction that requires external heat for the reaction to occur. The heat required to produce enough hydrogen varies with the demand put on the fuel cell system at any given point in time. Accordingly, the heating means for the fuel processor must be capable of operating over a wide range of heat outputs. Heating the fuel processor with heat generated externally from either a flame combustor or a catalytic combustor is known. U.S. patent applications Ser. Nos. 08/975,422 and 08/980,087 filed in the name of William Pettit in November, 1997, now U.S. Pat. No. 5,887,276 and 6,077,620, respectively and assigned to the assignee of the present invention, disclose an improved catalytic combustor, and the integration thereof with a fuel cell system which fuels the combustor with unreformed liquid fuel, hydrogen-containing anode exhaust gas from the fuel cell, or both. The operating cycle depends on many factors, such as anode stoichiometry, steam/carbon ratio, electrical demand placed on the system, etc.

Thus, load changes placed on the fuel cell resulting in greater or lower power output requirements, requires the fuel processor to generate more or less hydrogen. Correspondingly, since the combustor generates whatever heat input is required to sustain the chemical reactions within the fuel processor, the combustor likewise must generate more or less heat to maintain the required reaction temperatures within the fuel processor. The control of heat production by the combustor is dependent upon several parameters, one of the principle ones being the fuel flow to the combustor, and particularly anode exhaust gas from the fuel cell.

A vehicular fuel cell system requires a fast response to fuel cell load changes. In some situations, the combustor may not be able to accept all of the anode exhaust gas being supplied. Prior control devices used to control hydrogen-containing gas which is not consumed by the anode demonstrate slow response times. Therefore, a problem results from the use of anode hydrogen-containing effluent gas as a fuel source to the combustor. Since the combustor is fueled by different sources, and in different modes, i.e., start-up, warm-up, running mode, conventional sensors which monitor overall anode effluent volume or mass flow do not account for the actual mass flow rate of hydrogen. Another problem is that actual mass flow rate of hydrogen to the fuel cell stack is difficult to accurately monitor on a real-time basis. The demand for hydrogen by the stack changes in response to fuel cell load changes which are often very rapid. Thus, it would be desirable to provide a hydrogen flow control method and apparatus which gives an accurate indication of hydrogen mass flow rate. It is also desirable to have such method and apparatus which has a fast response.

A further problem posed by fuel cell systems is the degradation of precious metal catalytic components of the electrode layers of the MEA. The catalytic sites become poisoned or occupied by carbon monoxide. Thus, reactive surface is lost due to carbon monoxide poisoning, and less reactive surface is available to catalyze fuel cell reaction of hydrogen and oxygen. Thus, it would be desirable to provide a method and apparatus to monitor the effect of carbon monoxide poisoning, and to detect progression of such poisoning before an excessive amount of catalytic reactive surface is rendered ineffective.

SUMMARY OF THE INVENTION

The present invention is an apparatus for monitoring a hydrogen-containing gas stream and optionally a non-hydrogen gas including carbon monoxide.

The apparatus includes a sensor assembly comprising at least two electrochemical cells or membrane electrode assemblies (MEAs) electrically isolated from one another and sequentially arranged in the path of a gas stream containing hydrogen. Each MEA includes a reactive surface area wherein hydrogen in the gas stream is sequentially passed over the reactive surface, is consumed, and a current is generated. The voltage of at least the first two sequential MEAs is regulated. Preferably, the potential of these MEAs is the same. The combined current generated by all of the sequential MEAs is proportional to the quantity of hydrogen consumed by the sensor and in the gas flow path entering the sensor.

The sensor assembly may used in combination with a laminar flow conduit whereby a portion of the hydrogen containing stream is diverted to the sensor and a current is generated.

The sensor may also be used in combination with a flow meter which measures the flow rate of the bulk gas stream in the laminar flow conduit from which the sensor receives a diverted stream therefrom. The amount of hydrogen in the diverted stream is proportional to the amount of hydrogen in the bulk gas stream in the laminar flow conduit.

The apparatus may also be used to monitor a non-hydrogen gas, such as carbon monoxide, by comparing the current generated by the individual MEAs.

BRIEF DESCRIPTION OF THE DRAWINGS

The various features, advantages and other uses of the present invention will become more apparent by referring to the following description and drawings in which.

DETAILED DESCRIPTION OF THE PREFERRED EMBODIMENTS

FIGS. 1–11 show a preferred apparatus for monitoring a hydrogen-containing gas stream according to the present invention.

In one aspect of the invention, the reaction between hydrogen and an oxidizer is conducted in a sensor which includes a sequential arrangement of pairs of opposing reactive catalytic surfaces which indicate the quantity of hydrogen present in the gas stream received by the sensor. Each pair of opposing reactive catalytic surfaces forms a part of a respective monitoring membrane electrode assembly (MEA). Through reaction of hydrogen and oxidizer at the sequential reactive surfaces, a current (amps) is produced by each MEA. The amount of current produced by the MEAs as a result of the reaction of hydrogen corresponds to the amount of hydrogen received and reacted in the sensor. The surface area of the respective reactive surface of each MEA is specifically selected and the voltage of each MEA is regulated, to ensure all of the hydrogen passing through the sensor is reacted or consumed. The arrangement is also useable to indicate the presence of non-hydrogen gas, such as carbon monoxide, which affects the reactive surfaces of the monitoring MEAs.

The apparatus for monitoring hydrogen, and optionally carbon monoxide is described herein with reference to components of a fuel cell system. The fuel cell system seen in FIG. 1 may be used, for example, in a vehicle (not shown) as an energy source for vehicle propulsion. In the system, a hydrocarbon is processed, for example, by reformation and gas shift reaction and preferential oxidation processes to produce a reformate gas which has a relatively high hydrogen content on a volume basis. Therefore, reference to hydrogen-rich, or relatively high hydrogen content, refers to such content on a volume basis which is a quantity interchangeable with molar basis to express relative amounts of constituents.

The invention is hereafter described in the context of a fuel cell fueled by a reformate prepared from methanol (MeOH). However, it is to be understood that the principles embodied herein are equally applicable to fuel cells generally, regardless of the fuel or hydrogen source used. There are other reformable hydrocarbon and hydrogen-containing fuels such as ethanol or gasoline, which are used to produce hydrogen.

Figure 1:
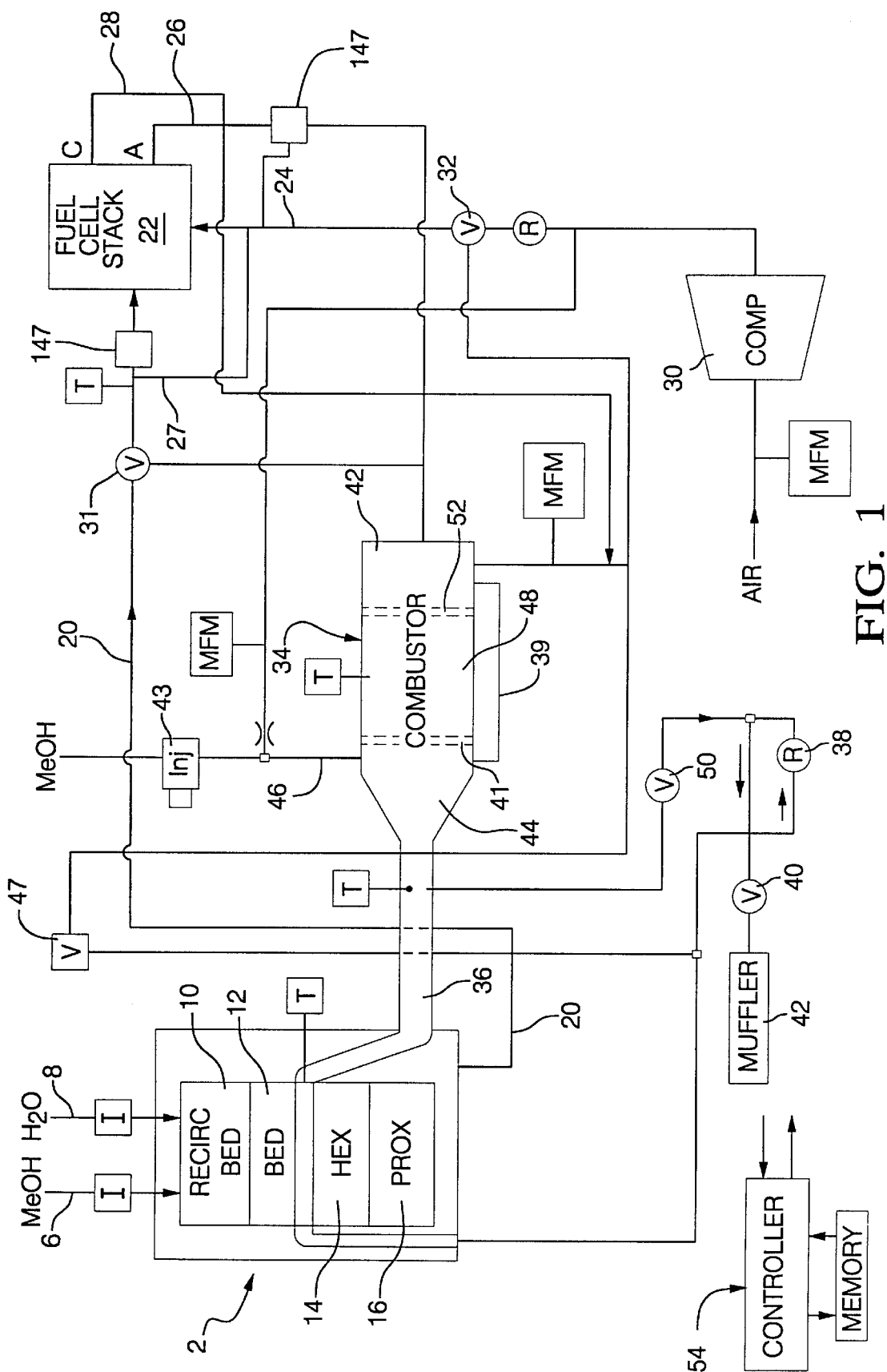
FIG. 1 is a flow diagram depicting a fuel cell apparatus including the hydrogen monitoring control apparatus of the present invention in two possible locations.
Figure 2:
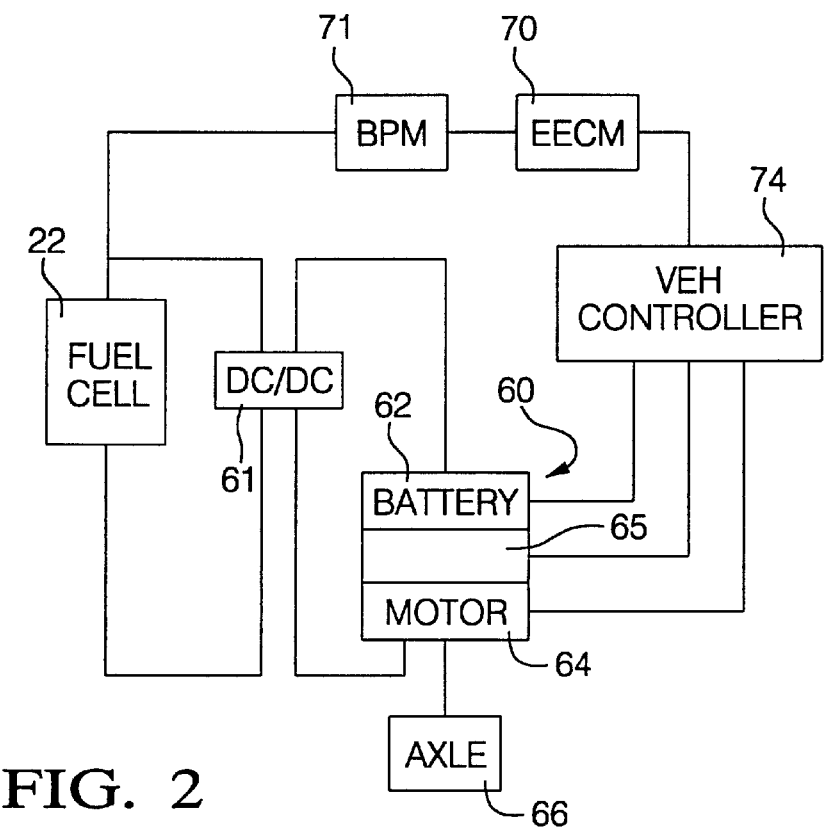
FIG. 2 is a flow diagram of the fuel cell apparatus shown in FIG. 1 connected in a pictorial representation of a use application.

As shown in FIG. 1, a preferred fuel cell apparatus includes a fuel processor 2 for catalytically reacting methanol from a methanol stream 6 and water or steam from a water stream 8 in a recirculating bed 10 and a catalytic bed 12 to form a hydrogen-rich reformate gas stream. A heat exchanger 14 is interposed between the catalytic bed 12 and a preferential oxidation (PROX) reactor 16. The reformate output gas stream comprises primarily $H_2$ and $CO_2$, but also includes $N_2$, CO and water. The reformate stream passes through the preferential oxidation (PrOx) reactor 16 to reduce the CO-levels therein to acceptable levels (i.e., below 20 ppm). The $H_2$ rich reformate stream 20 is then fed through valve 31 into the anode chamber of a fuel cell 22. At the same time, oxygen (e.g., air) from an oxidant stream 24 is fed into the cathode chamber of the fuel cell 22. The hydrogen from the reformate stream 20 and the oxygen from the oxidant stream 24 react in the fuel cell 22 to produce electricity. In addition, oxygen (air bleed) in line 27 is added to the $H_2$-rich reformate stream 20 just before the fuel cell 22. This air line 27 also provides air to the gas monitoring apparatus 147.

Anode exhaust or effluent 26 from the anode side of the fuel cell 22 contains some unreacted hydrogen. The cathode exhaust or effluent 28 from the cathode side of the fuel cell 22 contains some unreacted oxygen. Air for the oxidant stream 24 is provided by a compressor 30 and is directed to the fuel cell 22 by a valve 32 under normal operating conditions. During start-up, however, the valve 32 is actuated to provide air to the input of a combustor 34 used to heat the fuel processor 2, as will be described in more detail hereinafter.

Heat from the heat exchanger 14 heats the catalyst bed(s) 10 and 12 in the fuel processor 2 and also heats the PrOx 16 during start up. In this regard, the $H_2O$—MeOH mixture supplied to the fuel processor 2 will be vaporized and preferably be recirculated/refluxed several times (e.g., 20×) through the recirculating bed 10 in the fuel processor 2, the heat exchanger side of the bed 12, the PrOx 16 and the heat exchanger 14 such that the mixture also functions as a heat transfer medium for carrying heat from the heat exchanger 14 into the beds 10 and 12 of the fuel processor 2 and to the PrOx 16.

The heat exchanger 14 itself is heated from exhaust gases 36 exiting the catalytic combustor 34. The gases 36 exiting the heat exchanger 14 are still hot and could be passed through an expander, not shown, which could drive the compressor 30 or utilized in another manner. In the present implementation, as shown in FIG. 1, the exhaust gases from the fuel processor 2 pass through a regulator 38, a shutoff valve 40 and a muffler 42 before being released to the atmosphere.

MeOH vapor 39 emanates from a vaporizer 41 nested in the exhaust end 44 of the combustor 34. The vaporizer 41 is a heat exchanger that extracts heat from the combustor 34 exhaust to vaporize a first fuel stream, such as liquid MeOH 46 provided to the vaporizer 41 by fuel metering device 43 from the vehicle's fuel tank. The MeOH vapor 39 exiting the vaporizer 41 and the anode effluent 26 are reacted in a catalyst bed 48 of the combustor 34 lying intermediate the inlet and exhaust ends 42 and 44 respectively of the combustor 34. Oxygen is provided to the combustor 34 either from the compressor 30 (i.e., via valve 32) or from a second air flow stream, such as a cathode effluent stream 28 depending on system operating conditions. A valve 50 permits releasing of the combustor exhaust 36 to the atmosphere when it is not needed in the fuel processor 2.

Further details concerning the construction of the combustor 34 can be had by referring to pending U.S. patent applications Ser. Nos. 08/975,422 and 08/980,087 filed in the name of William Pettit in November 1997, the entire contents of which are incorporated herein by reference.

An electric heating element 52 is provided upstream of the catalyst bed 48 in the combustor 34 and serves to vaporize the liquid fuel 46 entering the combustor 34, heat the gas entering the bed 48 as well as preheating the bed 48 during start-up of the combustor 34. The heating element 52 may or may not be catalyzed. After start-up, as described hereafter, the electric heater 52 is no longer required since the fuel will be vaporized by the exhaust gases emanating from the exhaust end 44 of the combustor 34. A preferred electric heater 52 comprises a commercially available, uncatalyzed extruded metal monolith resistance element such as is used to light off the catalyst of a catalytic converter used to treat IC engine exhaust gases.

The exhaust end 44 of the combustor 34 includes a chamber that houses the vaporizer 41 which is a coil of metal tubing which is used to vaporize liquid fuel to fuel the combustor 34. More specifically, under normal post-start-up conditions, air or cathode effluent 28 may be introduced into the inlet end of the coil and mixed with liquid fuel sprayed into the inlet end via a conventional automotive type fuel injector. The airborne atomized fuel passes through the several turns of the heated coil tube, and therein vaporizes and exits the tube at an outlet which is located in the cathode effluent supply conduit. This vaporized first fuel stream supplements a second fuel stream or anode effluent 26 as fuel for the combustor 34 as may be needed to meet the transient and steady state needs of the fuel cell apparatus. The vaporizer coil is sized to vaporize the maximum flow rate of fuel with the minimum combustor exhaust flow rate, and is designed to operate at temperatures exceeding the autoignition temperature of the MeOH-air mixture therein throughout its fuel operational range. Autoignition within the vaporizer is avoided, however, by insuring that the velocity of the mix flowing through the coil significantly exceeds the worst-case flame speed of the mixture which varies with the composition of the inlet streams.

The amount of heat demanded by the fuel processor 2 which is to be supplied by the combustor 34 is dependent upon the amount of fuel input and ultimately the desired reaction temperature in the fuel processor 2. To supply the heat demand of the fuel processor 2, the combustor 34 utilizes all anode exhaust or effluent 26 and potentially some liquid fuel. Enthalpy equations are used to determine the amount of cathode exhaust 28 or air to be supplied to the combustor 34 to meet the desired temperature requirements of the combustor 34 and ultimately to satisfy the fuel processor 2. The oxygen or air provided to the combustor 34 includes one or both of cathode effluent exhaust 28 which is typically a percentage of the total oxygen supplied to the cathode of the fuel cell 22 and a compressor output air stream depending on whether the apparatus is operating in a start-up mode wherein the compressor air stream is exclusively employed or in a run mode using the cathode effluent 28 and/or compressor air. In the run mode, any total air, oxygen or diluent demand required by the combustor 34 which is not met by the cathode effluent 28 is supplied by the compressor 30 in an amount to balance the enthalpy equations to reach the desired reaction temperature within the combustor 34 so as to supply the amount of heat required by the fuel processor 2 at the desired temperature. The air control is implemented via an air dilution valve 47 which is a stepper motor driven valve having a variable orifice to control the amount of bleed-off of cathode exhaust supplied to the combustor 34.

The fuel cell apparatus of FIG. 1 operates as follows. At the beginning of operations when the fuel cell apparatus is cold and starting up: (1) the compressor 30 is driven by an electric motor energized from an external source (e.g., a battery) to provide the necessary system air; (2) air is introduced into the combustor 34 as well as the input end of the vaporizer 41; (3) liquid fuel 46 (e.g., MeOH) is injected into the inlet end of the vaporizer 41 via a fuel injector, and atomized as fine droplets with the air flowing therein; (4) the air-MeOH droplet mix exits the vaporizer 41 and mixes with compressor air introduced into the combustor 34, and is then introduced into the input end 42 of the combustor 34; (5) the mix passes through a flame arrestor in the front of the combustor 34; (6) the mix is then heated by the heater 52 to vaporize the liquid droplets and heat the mixture; (7) the preheated vaporous mix then enters a mixing-media bed for still further intimate mixing before contacting the light-off catalyst bed; (8) upon exiting the mixing-media bed, the mix begins oxidizing on the light-off catalyst bed just before it enters a primary catalyst bed 48, or reacting section of the combustor 34, where substantially complete combustion of the fuel is effected; and (9) the hot exhaust gases exiting the catalyst bed are conveyed to the heat exchanger 14 associated with the fuel processor 2.

Once the fuel processor temperature has risen sufficiently to effect and maintain the reformation process: (1) valve 32 is activated to direct air to the cathode side of the fuel cell 22; (2) MeOH and water are fed to the fuel processor 2 to commence the reformation reaction; (3) reformate exiting the fuel processor 2 is fed to the anode side of the fuel cell 22; (4) anode effluent 26 from the fuel cell 22 is directed into the combustor 34; (5) cathode effluent 28 from the fuel cell 22 is directed into the combustor 34; (6) air is introduced into the vaporizer 41; (7) liquid methanol is sprayed into the vaporizer 41; (8) the methanol-air mix circulates through the heated vaporizer coil where the MeOH vaporizes; (9) the methanol-air mix along with the cathode effluent 28 then mixes with the anode effluent 26; and (10) the mix is burned on the catalyst bed of the combustor 34.

During normal (i.e., post start-up) operating conditions, the heater 42 is not used as the vaporizer 41 alone vaporizes the MeOH and preheats the MeOH-air mix. Under certain conditions, as described hereafter, the combustor 34 could operate solely on the anode and cathode effluents, without the need for additional MeOH fuel from the vaporizer 41. Under such conditions, MeOH injection to the combustor 34 is discontinued. Under other conditions, e.g., increasing power demands, supplemental fuel is provided to the combustor 34.

As described above, the combustor 34 receives multiple fuels, such as a methanol-air mix as well as anode effluent 26 from the anode of the fuel cell 22. Oxygen depleted exhaust air 28 from the cathode of the fuel cell 22 and air from the compressor 30 are also supplied to the combustor 34.

According to the present fuel cell example, a controller 54 shown in FIG. 1 controls the operation of the combustor 34. Anode exhaust or effluent 26 plus a liquid fuel, i.e., methanol, if required, support the energy requirements of the combustor 34. An enthalpy balance maintains the desired reaction by temperature controlling the amount of air and/or cathode exhaust supplied to the combustor 34 to meet all fuel processor heat requirements.

It should be noted that the energy requirements of the apparatus components are expressed herein in terms of power. This is for convenience and is meant to express an energy rate, often in units of kilowatts, rather than BTU per second.

The controller 54 may comprise any suitable microprocessor, microcontroller, personal computer, etc., which has a central processing unit capable of executing a control program and data stored in a memory. The controller 54 may be a dedicated controller specific to the combustor 34 or implemented in software stored in the main vehicle electronic control module. Further, although the following description describes a software based control program for controlling the combustor 34 in various modes of operation or sequence, it will also be understood that the combustor control can also be implemented in part or whole by dedicated electronic circuitry.

The controller 54 controls the operation of the combustor 34 in six different modes or sequences of operation. The separate modes of operation include (1) combustor start-up, (2) combustor operation during fuel processor warm-up, (3) combustor operation during fuel processor start-up, with the fuel cell off-line, (4) combustor operation during fuel processor run mode with the fuel cell stack on-line, and (5) combustor shutdown.

Further details concerning the construction and operation of the above-described fuel cell apparatus can be had by referring to co-pending U.S. patent application Ser. No. 09/358,080, filed on Jul. 21, 1999, in the names of David J. Hart-Predmore and William H. Pettit, and entitled "Methanol Tailgas Combustor Control Method", the entire contents of which are incorporated herein by reference.

The fuel cell system generally includes the fuel cell 22 as part of an external circuit 60 (see FIG. 2) wherein a portion of the external circuit 60, comprises a battery 62, an electric motor 64 and drive electronics 65 constructed and arranged to accept electric energy from a DC/DC converter 61 coupled to the fuel cell 22 and to convert the DC power to mechanical energy from the motor 64. The battery 62 is constructed and arranged to accept and store electrical energy supplied by the fuel cell 22 and to provide electric energy to motor 64. The motor 64 is coupled to driving axle 66 to rotate wheels of a vehicle (not shown). An electrochemical engine control module (EECM) 70 and a battery pack module (BPM) 71 monitor various operating parameters, including, but not limited to, the voltage and current of the stack which is done by the battery pack module 71, for example. The BPM 71 sends an output signal (message) to the vehicle controller 74 based on conditions monitored by the BPM 71. The vehicle controller 74 controls operation of the battery 62, the drive electronics 65 and the electric motor 64 in a conventional manner.

The controller 54 which may be implemented in the BPM 71 and/or the EECM 70, monitors the operation of fuel cell system with respect to pressures, temperatures, startup times, cycles, etc., and routinely generates signals in response to conditions of the system.

The hydrogen monitoring apparatus according to the present invention may be implemented in either hardware or software. Preferably, the control is implemented in software as part of the control program of the controller 54. However, the following description will be understood to be by convenience only for clarity in illustrating and describing the function of the inventive hydrogen monitoring system. The apparatus for monitoring a hydrogen containing gas stream, and optionally carbon monoxide has components which are structurally similar to the MEA portion of a fuel cell.

Figure 3:
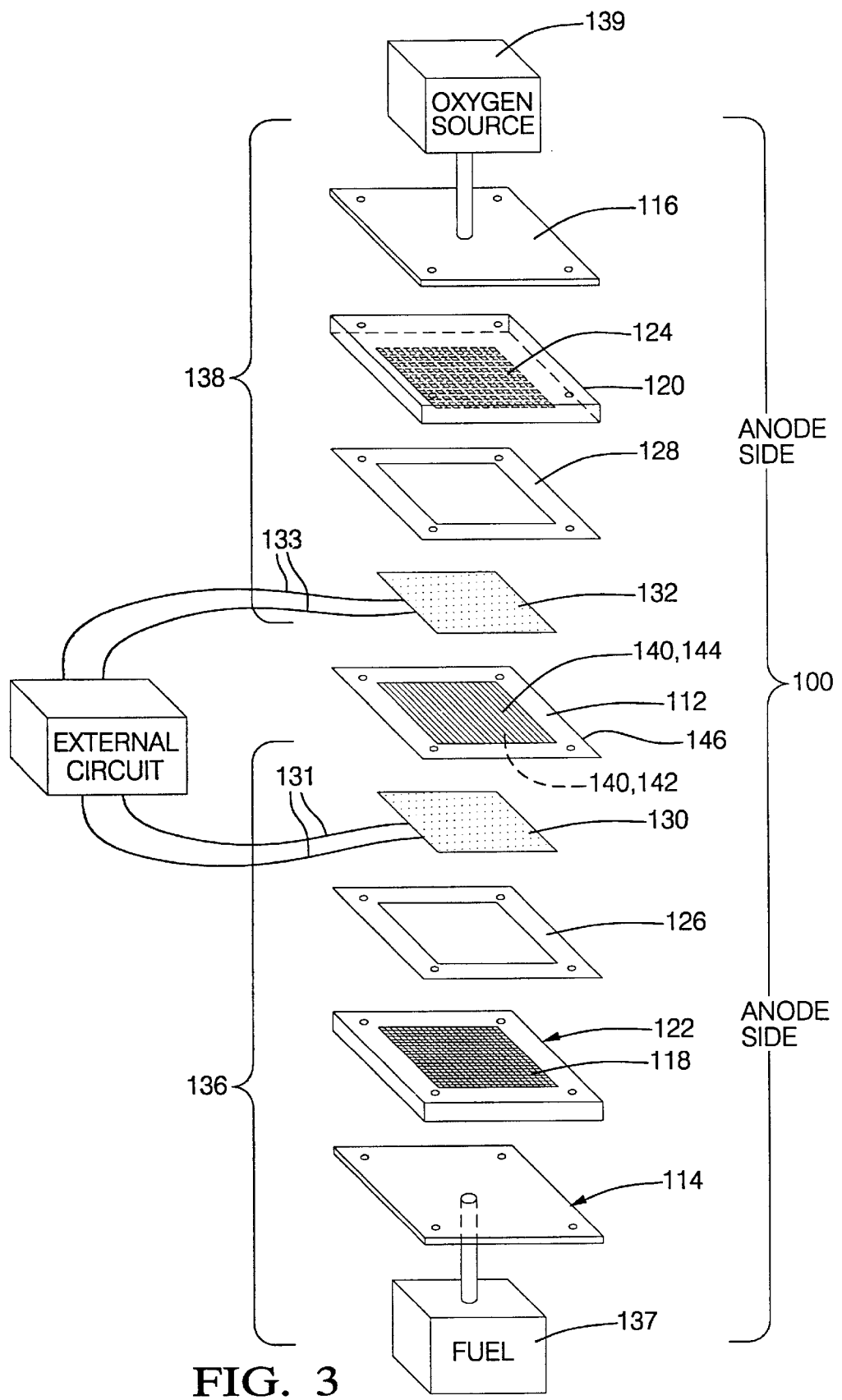
FIG. 3 is an exploded view of an electrochemical fuel cell having a membrane electrode assembly.

FIG. 3, shows a pictorial representation of a fuel cell 100 with a combination membrane electrode assembly (MEA) 112 incorporated therein. Cell 100 comprises stainless steel endplates 114, 116, graphite blocks 118, 120 with openings 122, 124 to facilitate gas distribution, gaskets 126, 128, carbon cloth current collectors 130, 132 with respective connections 131, 133 and the (MEA) 112. The two sets of graphite blocks, gaskets, and current collectors, namely 118, 126, 130 and 120, 128, 132 are each referred to as respective gas and current transport means 136, 138. Anode connection 131 and cathode connection 133 are used to interconnect with an external circuit which may include other fuel cells. Fuel cell 100 includes gaseous reactants, one of which is a fuel supplied from fuel source, 137, and another is an oxidizer supplied from source 139. The gases from sources 137, 139 diffuse through respective gas and current transport means 136 and 138 to opposite sides of the MEA 112.

Figure 4:
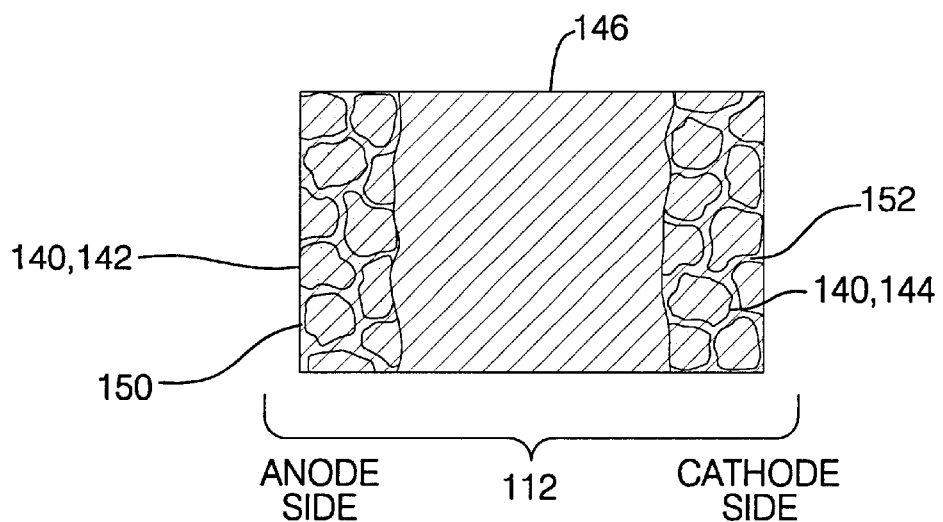
FIG. 4 is an enlarged illustration of a cross-section of a membrane electrode assembly.

FIG. 4 shows a cross sectional view of the membrane electrode assembly (MEA) 112. Referring to FIG. 4, porous electrodes 140 form anode 142 at the fuel side and cathode 144 at the oxygen side. Anode 142 is separated from cathode 144 by a proton exchange membrane 146. The membrane 146 provides for ion transport to facilitate reactions in the fuel cell 100. Catalyzed carbon particles 150 on the anode side and catalyzed carbon particles 152 at the cathode side form reactive surfaces.

In the fuel cell membrane 146 is a cation permeable, proton conductive membrane, having H+ or $H_3O_+$ ions as the mobile ion; the fuel gas is hydrogen and the oxidant is oxygen or air. The overall cell reaction is the oxidation of hydrogen to water and the respective reactions at the anode 142 and cathode 144 are as follows:

$$H_2 = 2H^+ + 2e$$

$$1/2 O_2 + 2H^+ + 2e = H_2O$$

Figure 5:
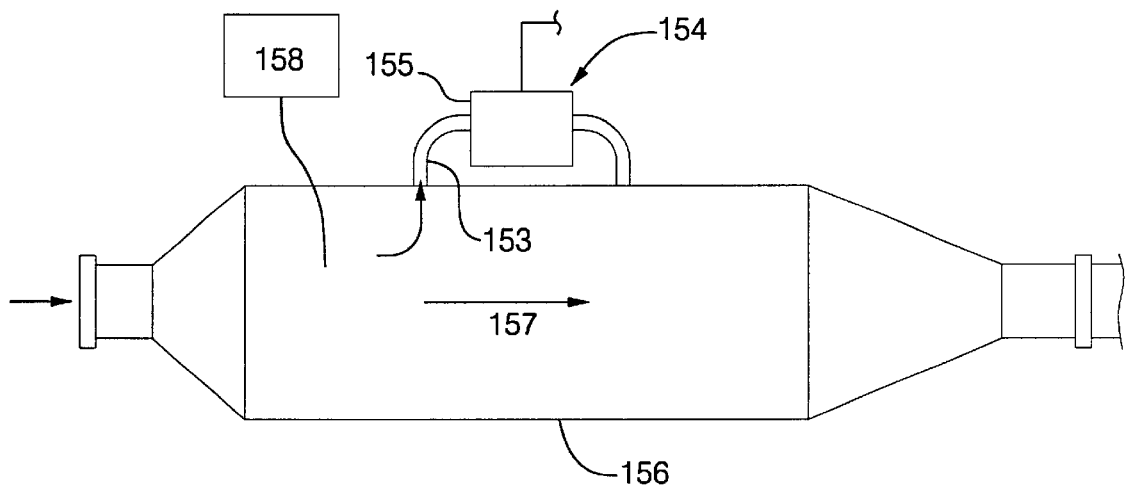
FIG. 5 is pictorial illustration of a hydrogen monitoring control apparatus in a use application.
Figure 6:
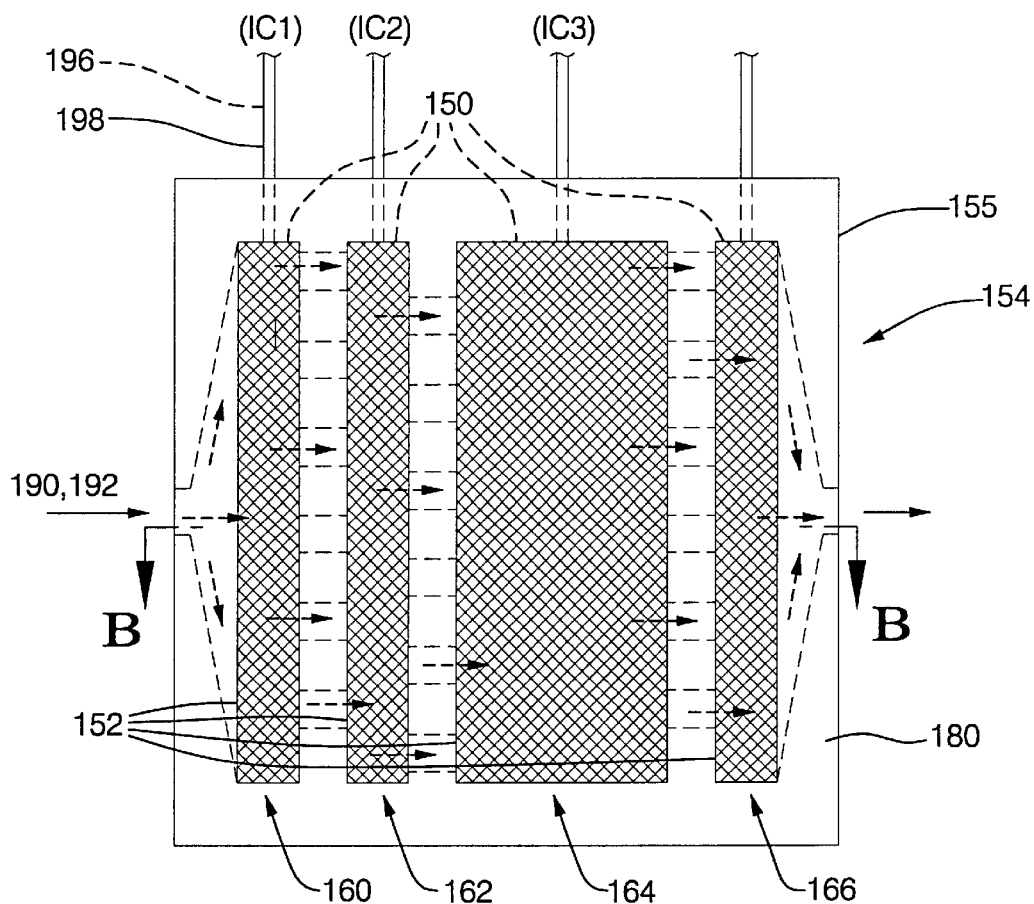
FIG. 6 is a front view taken in the direction of arrow A in FIG. 8.
Figure 7:
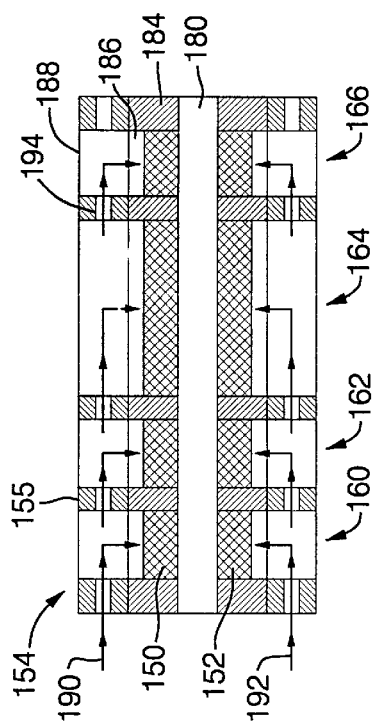
FIG. 7 is an enlarged cross sectional view taken along lines BB in FIG. 6.

FIGS. 5–7 show a preferred device, the gas monitoring apparatus 147, for monitoring a hydrogen containing gas stream and optionally a non-hydrogen gas such as carbon monoxide, comprising a container 155 housing a sensor assembly 154 which contains the sequential MEAs each having an opposed anode reactive surface 150, and a cathode reactive surface 152. The sensor assembly 154 is preferably used in combination with a laminar flow conduit 156 in fluid flow communication with the sensor, and a flow meter 158 for indicating the flow of the bulk stream in the laminar conduit 156.

Figure 8:
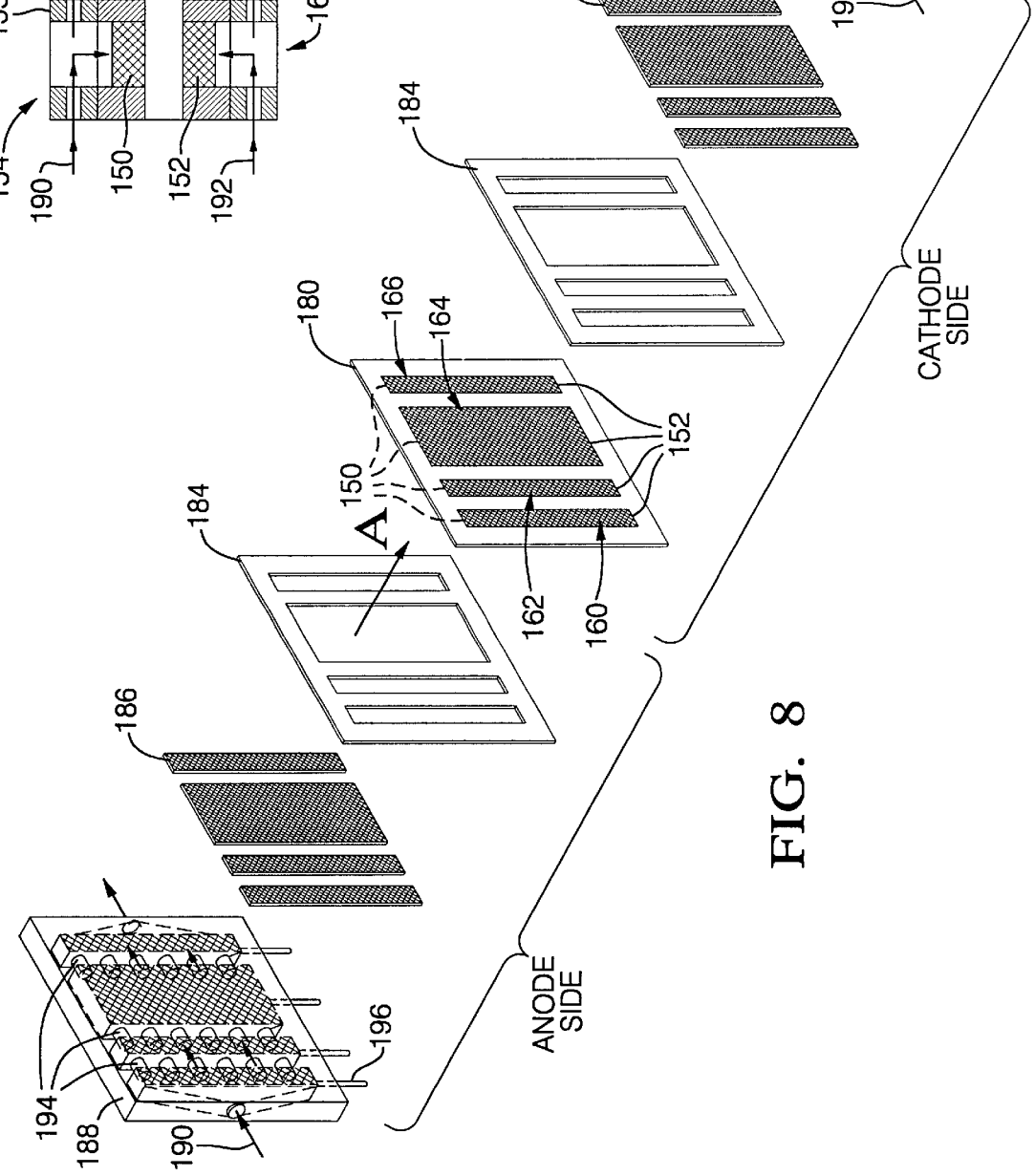
FIG. 8 is an exploded view of the hydrogen monitoring control apparatus of FIG. 5.

As best seen in FIG. 7, the reactive surface areas 150 and 152 of a particular MEA are of the same area and are aligned on opposite sides of a separator 180 as shown in FIGS. 7 and 8. As the reactive surfaces 150 and 152 on a particular MEA are of the same size and are oppositely aligned on either side of separator 180, it is understood by those skilled in the art that when describing features of electrode reactive surface areas such as 150, 152, it is only necessarily to express the surface area feature based on either of the surfaces, here 150 or 152. As such, for convenience, the reactive surfaces 150 and 152 for a single cell or MEA will collectively be referred to as "surface area 150, 152."

The apparatus shown in FIGS. 5–7 can be used in a variety of different arrangements. In one embodiment, the sensor 154 is used in combination with a laminar flow conduit 156. In this application, the laminar flow conduit 156 preferably replaces a portion of a bulk reformate stream 20 or anode effluent stream 26 as seen in FIG. 1. As best seen in FIG. 5, a diverted stream 153 is channeled from the laminar flow conduit 156 to and through sensor 154 and back to the laminar flow conduit 156. In the case of laminar flow, there will be an essentially constant proportionality between the amount of gas, or hydrogen in the diverted stream 153 to the container 155 and the amount of the bulk gas stream 157 in the laminar flow conduit 156. In this embodiment, the combined current obtained by the reaction between hydrogen and the oxidizer at the reactive surface areas 150, 152 of the MEAs 160, 162, 164, 166 is proportional to the amount of hydrogen consumed in the sensor 154 according to Faraday's Law. According to Faraday's Law, for every reacting hydrogen molecule there are two electrons produced. The Law is expressed according the Equation: $m = I \cdot M/z \cdot F$. In the Equation, m (grams per second) is the mass flow of hydrogen to the sensor; I (amps) is the current produced by the sensor; M (grams per mole) is the mole mass of hydrogen; z represents two electrons per molecule of hydrogen; and F (coulombs per mole) is the Faraday constant.

As seen in FIGS. 5–7, by the reaction of hydrogen and oxidizer at the reactive surface areas of the sequential MEAs, 160, 162, 164, 166 and the combined resulting current produced by the MEAs, the mass flow of hydrogen is obtained for the diverted stream 153. The ability to determine the mass flow rate of hydrogen in a diverted stream through measure of current provides a mechanism to establish a performance or characteristic chart, known by those skilled in the field as a look up table, to accurately determine the mass flow rate of hydrogen in the bulk gas stream in the laminar flow conduit 156. For example, a look up table may provide a range of current (amps) values for a specific sensor assembly 154, and a laminar flow conduit 156. In operation, an operator recording the current from sensor 154 can reference the look up table and determine the pre-established value or range of values of the mass flow rate of hydrogen in the laminar flow conduit 156.

Referring now to FIG. 5, in an alternate embodiment, the sensor is used in combination with a laminar flow conduit 156 as described, and a flow meter 158 which indicates the actual flow rate of the bulk gas stream 157 in the laminar flow conduit 156. As described, a portion of the bulk gas stream 157 in the laminar flow conduit 156 is channeled into a diverted stream 153 to a container 155 which houses the sensor 154 assembly components. As described, the quantity of hydrogen in the diverted stream 153 is monitored by the sensor 154 in proportion to the current produced by the sensor 154 as hydrogen is consumed therein at the reactive surface 150, 152 of the respective MEAs 160, 162, 164 and 166 as seen in FIGS. 6 and 7. This quantity of hydrogen consumed by the sensor 154 from the diverted stream 153 is then related to the total quantity of hydrogen in the bulk gas stream 157 in the laminar flow conduit 156 according to the proportionality between the diverted stream 153 and the bulk stream 157. By this arrangement, through use of the sensor 154, laminar conduit 156 and flow meter 158, it is possible to determine the overall flow rate and to more accurately calculate the mass flow rate of hydrogen in the bulk stream 157 in the laminar flow conduit 156. Therefore, the quantity or mass flow of hydrogen is ascertainable in the exemplary reformate stream 20 or anode effluent stream 28 of the fuel cell system of FIG. 1.

Although the use of a single flow meter 158 has been described and shown, it is understood the placement and quantity of flow meters 158 may vary without departing from the present invention. For example, a second flow meter may be placed in the diverted stream 153 to establish or confirm the proportion of gas diverted from the bulk stream 157 in laminar flow conduit 156.

The reactive surface 150, 152 of each MEA 160, 162, 164, 166 in the sensor 154 is preferably arranged as shown in FIGS. 6–8. FIGS. 6–8 show four independent, electrically isolated membrane electrode assemblies (MEAs) or cells 160, 162, 164, 166 arranged sequentially with respect to gas flow paths 190 and 192 indicated by the arrows in FIGS.

6–8. Preferably, gas path or flow 192 is reformate gas stream 20 or anode effluent 26 and path 192 is an oxidant stream 24 or cathode effluent stream 28 as shown in FIG. 1. Each MEA or cell has an anode reactive surface 150 opposite a cathode reactive surface 152. The area of the reactive surface 150, 152 of the first 160 and second 162 MEAs is essentially equivalent.

Figure 11:
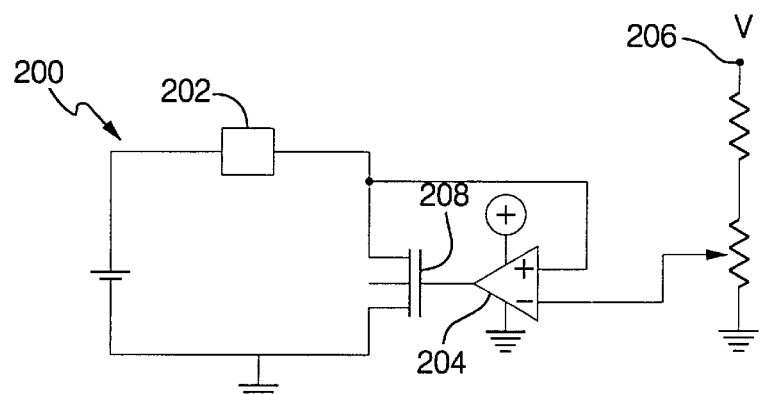
FIG. 11 is a schematic of an electrical circuit for a current sensor and voltage regulator device.

Referring to FIGS. 6 and 11, by example only, each MEA, and more particularly, each of the first two MEAs 160, 162 current is measured and voltage is regulated by a regulator device 200 shown in FIG. 11. As described, current is generated at each MEA by reaction of hydrogen and the oxidizer at the reactive surface 150, 152 and is detected by a current sensor 202 Voltage from the respective MEA is directed to a differential amplifier 204 and the MEA voltage is compared to a preselected referenced voltage 206 from a source independent of the MEA. The voltage from the respective MEA is thereafter regulated through a transistor 208 as shown to maintain the voltage of each of the respective MEAs in accord with a selected respective reference voltage 206.

Preferably, the voltage potential of each of the first 160 and second 162 MEAs is held constant at essentially the same level, as shown and described, by use of a regulator device 200. By this preferred arrangement, in a nominal operating condition, the current produced by the first 160 and second 162 MEAs is the same or of a known level (calibration). Referring now to FIGS. 6–8, if the current (IC1) produced by the first MEA 160 is greater than the current (IC2) produced by the second MEA 162 this would indicate that there is an insufficient amount of hydrogen in the gas flow path 190 remaining after consumption thereof at the first MEA 160. This would provide an indication that the amount of hydrogen in the stream 190 is relatively low. If the current produced by the first MEA (IC1) 160 is less than the current produced by the second MEA (IC2) 162 this is an indication that the catalytic reactive surface 150, 152 of the first MEA 160 is poisoned, fouled or otherwise occupied by non-hydrogen components of the gas stream such as carbon monoxide.

The third MEA 164 preferably has a reactive surface area 150, 152 greater than the reactive surface area of the second MEA 162. It is preferred that the third MEA 164 be held at essentially an open circuit potential or very low voltage potential. The regulation of voltage on the third MEA 164 is preferably achieved through use of a regulator device 200 previously described. In this arrangement, the amount of current produced by the third MEA 164 may be very large. In other words, a very large quantity of hydrogen is consumable by the third MEA 164 by virtue of its large reactive surface area and low potential. The fourth MEA 166 downstream of the third MEA 164 theoretically should register no potential and no current if the selection of size of the reactive surface 150, 152 of the first three MEAs 160, 162, 164 has been properly made. The fourth MEA 166 is merely an indicator to show that all the hydrogen has been consumed. In this arrangement, the sum of the currents produced at the first, 160 second 162 and third 164 MEAs corresponds directly to the amount of hydrogen consumed at the collective reactive surface 150, 152 of the first three MEAs 160, 162 and 164.

Figure 9:
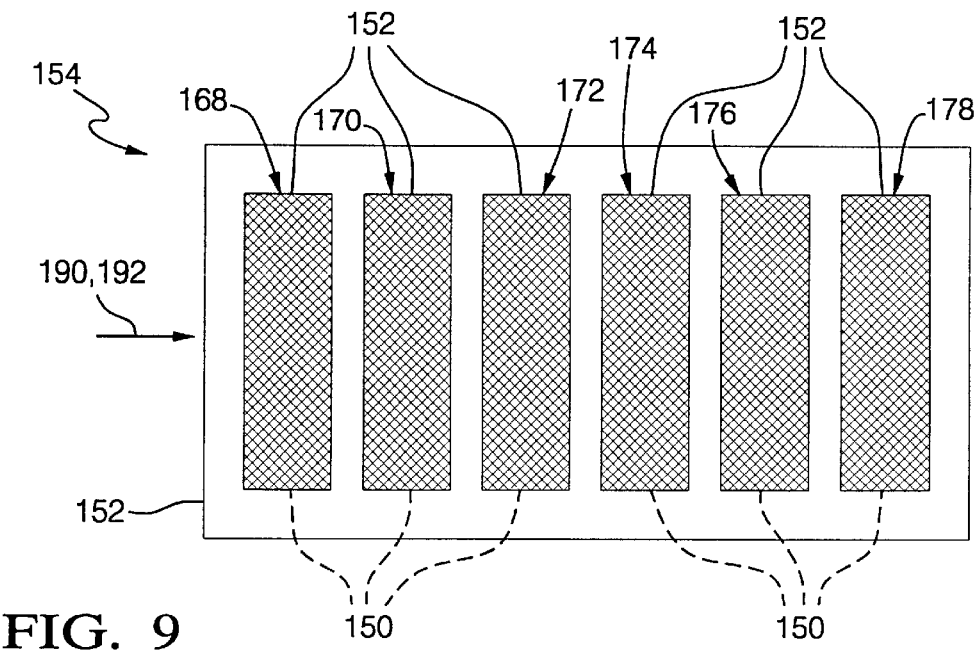
FIG. 9 is a pictorial illustration of a hydrogen monitoring control apparatus in an anode exhaust use application.
Figure 10:
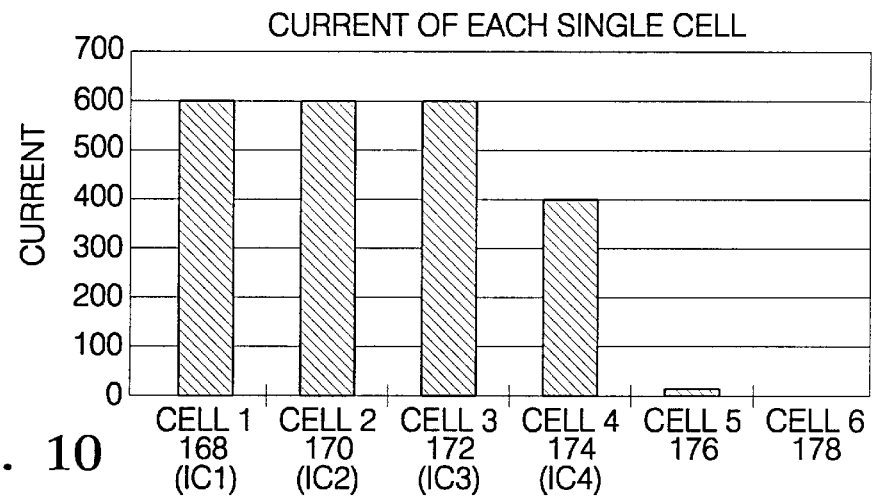
FIG. 10 is a graphic table depicting the current measured from the individual membrane electrode assemblies in the hydrogen monitoring control apparatus of FIG. 9.

Another arrangement of sequential MEAs is shown in FIG. 9. Here, six MEAs 168, 170, 172, 174, 176 and 178 are arranged in series with respect to the gas flow paths 190, 192 through the sensor 154. The reactive surface 150, 152 of the first 168 and second 170 MEAs are essentially the same and these MEAs are also held at essentially the same potential by regulator devices 200 as described in order to provide the indication of hydrogen deficiency or excess carbon monoxide as earlier described. The third through sixth MEAs 172, 174, 176, 178 each have a reactive surface 150, 152 which may be the same as or different from the areas of the first two MEAs 168, 170. The amount of reactive surface area of the third through sixth MEAs 172, 174, 176, 178 is not critical. The function of these last four MEAs in the series is to consume all of the hydrogen in the stream flowing through the sensor and provide a corresponding current output. These reactive surfaces must be of an area adequate to consume all of the hydrogen flowing through the sensor in order to accurately monitor the quantity of hydrogen. It is preferred that the number and area of reactive surfaces be selected so that all of the hydrogen is consumed before the stream comes in contact with the last reactive surface of the last MEA. An exemplary chart of the current produced by the MEAs in the arrangement of FIG. 9 is shown in FIG. 10.

It is also to be understood that more than the first two MEAs in a sequential series of MEAs along a flow path may be held at the same potential and have essentially the same reactive surface area 150, 152 in order to provide an indication of carbon monoxide fouling and/or low quantity of hydrogen.

The specific arrangement and construction of the preferred sensor 154 will now be described with reference to FIGS. 5–8. As shown, a sensor 154 assembly comprises a container 155 which houses a polymer membrane 180 which functions as a separator. Membrane 180 functions similar to membrane 146 previously described as shown in FIG. 3. The polymer membrane 180 is imprinted with distinct catalytically reactive surfaces or areas 150, 152 on opposing sides of membrane 180. Each pair of opposing reactive surface areas 150, 152 forms a distinct and electrically isolated MEA or cell. The reactive surface area 150, 152 for each MEA is essentially the same as the electrodes of the earlier described MEA 112. These pairs of catalytic reactive surface areas 150, 152 are electrically isolated from one another through use of gaskets 184 and arranged sequentially with respect to the flow of gas streams 190, 192. This arrangement essentially provides a plurality of individual MEAs or cells 160, 162, 164, 166 arranged in a series along the membrane 180.

As seen in FIGS. 7 and 8, graphitic/carbon paper diffusion layers 186 are arranged on the reactive surfaces 150, 152 between the open areas of the gasket 184. Finally, gas diffusion elements 188 are provided for feeding the hydrogen-containing gas stream 190 to the anode side of the membrane 180 and the oxidizing gas stream 192 to the cathode side of the membrane 180. As shown in FIGS. 6 and 7, gas flow passages 194 are provided between the respective MEAs, and in one arrangement, are essentially channeled through the insulating thin polymer membrane 180 between the MEAs (not shown). Respective connectors 196, 198 are provided in contact with each of the electrically isolated MEAs to direct signals to and from each MEA, from for example, a regulator device 200 and/or controller 54. These connectors provide access for voltage regulating and monitoring and for current monitoring. In one embodiment, a controller 54 as shown in FIG. 1, performs all the functions of voltage regulation, current monitoring and calculation of values relating to the sensor 154 and the preferred gas flow meter 158.

Referring back to FIGS. 1 and 5 the laminar flow conduit 156 and the associated sensor 154 may be located upstream, from the fuel cell stack 22, for example, between air bleed line 27 and the fuel cell stack 22. In this arrangement, the hydrogen monitoring apparatus of the present invention provides the ability to regulate hydrogen output from the fuel processor 2. This application also provides the ability to monitor the mass flow of hydrogen remaining in the anode effluent gas stream 26. This is accomplished by monitoring the current produced by the fuel cell stack 22 and by monitoring the mass flow of hydrogen in the reformate stream 20 before the stack through sensor 154 as described, and determining by difference the amount of hydrogen remaining in the anode effluent stream 26. In another arrangement, the apparatus of the invention is located in the anode effluent stream 26 of the stack 22 to regulate the amount of hydrogen being provided to the catalytic combustor 34. In this arrangement, if the amount of hydrogen in the anode effluent 26 is more than required to be consumed by the catalytic combustor 34, an amount of excess hydrogen may be sent to storage or vented to the atmosphere as previously described if desired.

As seen in FIGS. 7 and 8, the source of oxidant stream 192 provided to the sensor 154 is not critical. It is possible to use effluent cathode gas 28 from the stack 22 or to use an ambient air stream from, for example, the compressor 30 as previously described.

As shown in FIGS. 6 and 7 a convenient arrangement of MEAs having a common membrane 180 is shown so that the reactive surface area 150, 152 of the MEAs or cells 160, 162, 164, 166 are coplanar. This arrangement is not essential. An alternative arrangement would have the reactive surface 150, 152 of each MEA arranged in sequence one behind the other or in any other desired arrangement so long as they are arranged in sequence relative to the gas flow path.

While this invention has been described in terms of certain embodiments thereof, it is not intended that it be limited to the above description, but rather only to the extent set forth in the following claims.

The embodiments of the invention in which an exclusive property or privilege is claimed are defined in the following claims.

What is claimed is:

1. A gas monitoring apparatus for monitoring hydrogen and optionally carbon monoxide in a gas stream comprising:
    a conduit in fluid flow communication with said gas stream, said conduit providing substantially laminar flow of said gas stream;
    a container in fluid flow communication with at least a portion of said gas stream in said conduit, said container housing at least two sequentially arranged, electrically isolated electrochemical cells, each of said cells having a first and a second reactive surface area, said container is arranged to cooperate with said cells to define a first and a second gas flow path, said first gas flow path is sequentially along said first reactive surface areas of said cells and said second gas path is along said second reactive surface areas of said cells;
    at least one regulator for regulating voltage of at least said first and said second cells;
    at least one current monitor arranged to detect a current produced by the reaction of hydrogen at said reactive surface area of said cells.

2. The gas monitoring apparatus of claim 1 wherein said first and second reactive surface areas of said first and second cells are essentially the same.

3. The gas monitoring apparatus of claim 1 wherein said first and second reactive surface areas of said first and second cells are different.

4. The gas monitoring apparatus of claim 1, further comprising means for determining the amount of hydrogen in said gas stream proportional to said current from said cells.

5. The gas monitoring apparatus of claim 4, wherein said means includes a flow meter in fluid flow communication with said gas stream.

6. The gas monitoring apparatus of claim 4, wherein said means includes a look up table.

7. The gas monitoring apparatus of claim 1, wherein said cells further comprise a polymer membrane between said first and said-second reactive surface areas of said cells, wherein said polymer provides for exchange of protons between said first and said second reactive surface area of each of said cells.

8. The gas monitoring apparatus of claim 1 further comprises a gas diffusion layer for sequentially diffusing said portion of said gas stream along said first flow and said second flow paths onto said first and said second reactive surface areas of said cells, said diffusion layer further comprises sequential gas flow passages between said cells.

9. The gas monitoring apparatus of claim 1, wherein said portion of said gas stream flows along said first gas flow path and wherein an oxidant gas stream flows along said second gas flow path.

10. The gas monitoring apparatus of claim 1 further comprising means for comparing the amount of said current produced by said first and said second cells.

11. The gas monitoring apparatus of claim 10 further comprises a signal generator which produces a signal when the amount of said current produced by said first cell is greater than the amount of said current produced by said second cell.

12. The gas monitoring apparatus of claim 10 further comprises a signal generator which produces a signal when the amount of said current produced by said first cell is less than the amount of said current produced by said second cell.

13. The gas monitoring apparatus of claim 1, further comprising a third cell downstream of said first and said second cells in said first and said second gas flow paths, said third cell includes a first and a second reactive surface area at least as great as said reactive surface areas of said first and said second cells and wherein said regulator maintains the voltage of said third cell at a level less than the voltage of said first and said second cells.

14. A gas monitoring apparatus for monitoring hydrogen and optionally carbon monoxide in a gas stream comprising:
    at least two electrically isolated, electrochemical cells arranged in sequence relative to a flow path of at least a portion of said gas stream, each of said cells having a reactive surface area;
    at least one regulator for regulating voltage of said cells; and
    at least one current monitor arranged to detect a current produced by the reaction of hydrogen at said reactive surface area of said cells.

15. The gas monitoring apparatus of claim 14, wherein said reactive surface area of a first and a second of said cells are approximately the same.

16. The gas monitoring apparatus of claim 14, wherein said reactive surface area of a first and a second of said cells are different.

17. The gas monitoring apparatus of claim 14, wherein said regulator maintains the voltage of a first and a second of said cells at approximately the same level.

18. The gas monitoring apparatus of claim 14 wherein said regulator maintains the voltage of said first and second cells at different levels.

19. The gas monitoring apparatus of claim 14 further comprises a container arranged to cooperate with said cells to define said gas flow path sequentially along said reactive surface area of said cells.

20. The gas monitoring apparatus of claim 14 further comprises means for determining the amount of hydrogen in said gas stream proportional to said current from said cells.

21. The gas monitoring apparatus of claim 20, wherein said means includes a flow meter in fluid flow communication with said gas stream.

22. The gas monitoring apparatus of claim 20, wherein said means includes a look up table.

23. The gas monitoring apparatus of claim 14 further comprises a third cell in said gas flow path downstream of a first and a second of said cells, said third cell having a reactive surface area at least as great as said first and said second cells, and wherein said regulator maintains the voltage of said third cell at a level less than the voltage of said first and said second cells.

24. The gas monitoring apparatus of claim 14 further comprises means for comparing the amount of current produced by a first and a second of said cells.

25. The gas monitoring apparatus of claim 24 further comprises a signal generator which produces a signal when the amount of said current produced by said first cell is greater than the amount of said current produced by said second cell.

26. The gas monitoring apparatus of claim 24 further comprises a signal generator which produces a signal when the amount of said current produced by said first cell is less than the amount of said current produced by said second cell.

* * * * *